(12) United States Patent
Suyama

(10) Patent No.: US 10,734,355 B2
(45) Date of Patent: Aug. 4, 2020

(54) ELECTRONIC CIRCUIT BOARD, LAMINATED BOARD, AND METHOD OF MANUFACTURING ELECTRONIC CIRCUIT BOARD

(71) Applicant: OLYMPUS CORPORATION, Tokyo (JP)

(72) Inventor: Takuro Suyama, Ina (JP)

(73) Assignee: OLYMPUS CORPORATION, Tokyo (JP)

(*) Notice: Subject to any disclaimer, the term of this patent is extended or adjusted under 35 U.S.C. 154(b) by 0 days.

(21) Appl. No.: 15/851,900

(22) Filed: Dec. 22, 2017

(65) Prior Publication Data

US 2018/0122776 A1 May 3, 2018

Related U.S. Application Data

(63) Continuation of application No. PCT/JP2015/068422, filed on Jun. 25, 2015.

(51) Int. Cl.
*H01L 25/065* (2006.01)
*H01L 23/12* (2006.01)
(Continued)

(52) U.S. Cl.
CPC .......... *H01L 25/0655* (2013.01); *A61B 1/051* (2013.01); *H01L 21/3065* (2013.01);
(Continued)

(58) Field of Classification Search
CPC ............. H01L 25/0655; H01L 21/3065; H01L 21/4803; H01L 21/52
(Continued)

(56) References Cited

U.S. PATENT DOCUMENTS 9,006,879 B2 4/2015 Kato et al.
2009/0321915 A1* 12/2009 Hu ...................... H01L 23/5389
257/690
(Continued)

FOREIGN PATENT DOCUMENTS

JP H11-076152 A 3/1999
JP 2002-151801 A 5/2002
(Continued)

OTHER PUBLICATIONS

International Search Report dated Oct. 6, 2015 issued in PCT/JP2015/068422.
(Continued)

*Primary Examiner* — Shaun M Campbell
(74) *Attorney, Agent, or Firm* — Scully, Scott, Murphy & Presser, P.C.

(57) ABSTRACT

An electronic circuit board includes: electronic components; a silicon board that is plate shaped, includes a wiring pattern provided on at least one of a surface and a reverse surface thereof, and includes recessed portions where the electronic components are individually mounted; and a supporting board that is layered over the reverse surface of the silicon board, and includes a wiring pattern provided on at least one of a surface and a reverse surface thereof. Side faces of the recessed portions are perpendicular to the surface of the silicon board, the wiring pattern is connected to at least one of the electronic components mounted in the recessed portions, via at least one of a via and a bottom surface electrode provided in of the at least one of the recessed portions, and the recessed portions penetrate through the silicon board.

8 Claims, 10 Drawing Sheets

(51) Int. Cl.
*A61B 1/05* (2006.01)
*H01L 23/13* (2006.01)
*H01L 23/14* (2006.01)
*H01L 21/3065* (2006.01)
*H01L 21/48* (2006.01)
*H01L 21/52* (2006.01)
*H01L 21/56* (2006.01)
*H01L 23/31* (2006.01)
*H01L 23/48* (2006.01)
*H01L 25/10* (2006.01)
*H01L 25/00* (2006.01)
*H01L 23/538* (2006.01)

(52) U.S. Cl.
CPC .......... *H01L 21/4803* (2013.01); *H01L 21/52* (2013.01); *H01L 21/56* (2013.01); *H01L 23/12* (2013.01); *H01L 23/13* (2013.01); *H01L 23/147* (2013.01); *H01L 23/3121* (2013.01); *H01L 23/3135* (2013.01); *H01L 23/481* (2013.01); *H01L 25/105* (2013.01); *H01L 25/50* (2013.01); *H01L 23/5385* (2013.01); *H01L 23/5386* (2013.01); *H01L 23/5389* (2013.01)

(58) Field of Classification Search
USPC .......................................................... 257/21
See application file for complete search history.

(56) References Cited

U.S. PATENT DOCUMENTS

| | | | |
|---|---|---|---|
| 2010/0060553 A1* | 3/2010 | Zimmerman | ....... H01L 25/0753 345/60 |
| 2012/0018895 A1* | 1/2012 | Oganesian | ............ H01L 23/481 257/773 |
| 2014/0231635 A1* | 8/2014 | Kerness | ................ G01S 17/026 250/226 |
| 2015/0069624 A1* | 3/2015 | Pham | .................. H01L 25/0652 257/774 |

FOREIGN PATENT DOCUMENTS

| | | |
|---|---|---|
| JP | 2003-209129 A | 7/2003 |
| JP | 2005-116943 A | 4/2005 |
| JP | 2005-317585 A | 11/2005 |
| JP | 2007-067215 A | 3/2007 |
| JP | 2011-228335 A | 11/2011 |
| JP | 2013-141028 A | 7/2013 |

OTHER PUBLICATIONS

Japanese Office Action dated May 21, 2019 in Japanese Patent Application No. 2017-524531.

* cited by examiner

ELECTRONIC CIRCUIT BOARD, LAMINATED BOARD, AND METHOD OF MANUFACTURING ELECTRONIC CIRCUIT BOARD

CROSS-REFERENCE TO RELATED APPLICATION

This application is a continuation of International Application No. PCT/JP2015/068422, filed on Jun. 25, 2015, the entire contents of which are incorporated herein by reference.

BACKGROUND

The present disclosure relates to an electronic circuit board, a laminated board, and a method of manufacturing the electronic circuit board.

Endoscopes have been widely used for various examinations in the medical field and the industrial field. Especially, medical endoscopes are widely used, because by insertion of an elongated and flexible insertion unit having a solid state imaging element provided at a distal end thereof into a body cavity of a subject, such as a patient, in-vivo images inside the subject are able to be acquired without incision of the subject, and further, curative treatment is able to be carried out by protrusion of a treatment tool from the distal end of the insertion unit, as necessary.

In an imaging device used in such an endoscope, generally: a light receiving surface of a CCD chip thereof is covered by cover glass; an inner lead of a TAB tape is connected to an electrode provided at an outer peripheral edge portion of the light receiving surface; and the CCD chip is connected to electronic components and an external information processing device (see, for example, Japanese Unexamined Patent Application, Publication No. H11-76152).

In recent years, the number of electronic components used in an imaging device has increased, but for reduction of burdens on subjects, decrease in diameters and decrease in lengths of distal ends of insertion units of endoscopes are demanded, and thus a technique for improving mounting density of electronic components has been desired.

As a technique for improving mounting density of electronic components, a technique of forming a recessed portion in a silicon board and mounting a mounted component in the recessed portion has been proposed (see, for example, Japanese Unexamined Patent Application, Publication No. 2002-151801).

Further, a technique of forming an opening in a metal core, blocking the opening by forming an insulating layer on at least one of principal surfaces of the metal core, and mounting an electronic component in the opening has been proposed (see, for example, Japanese Unexamined Patent Application, Publication No. 2013-141028).

SUMMARY

An electronic circuit board according to one aspect of the present disclosure includes: electronic components; a silicon board that is plate shaped, includes a wiring pattern provided on at least one of a surface and a reverse surface thereof, and includes recessed portions where the electronic components are individually mounted; and a supporting board that is layered over the reverse surface of the silicon board, and includes a wiring pattern provided on at least one of a surface and a reverse surface thereof, wherein side faces of the recessed portions are perpendicular to the surface of the silicon board, the wiring pattern is connected to at least one of the electronic components mounted in the recessed portions, via at least one of a via and a bottom surface electrode provided in of the at least one of the recessed portions, and the recessed portions penetrate through the silicon board.

The above and other features, advantages and technical and industrial significance of this disclosure will be better understood by reading the following detailed description, when considered in connection with the accompanying drawings.

DETAILED DESCRIPTION

In the following description, as modes for carrying out the present disclosure (hereinafter, referred to as "embodiments"), electronic circuit boards, a laminated board having electronic circuit boards layered over each other, and methods of manufacturing the electronic circuit boards will be described. Further, the present disclosure is not limited by these embodiments. Furthermore, the same portions are assigned with the same reference signs, throughout the drawings. Moreover, the drawings are schematic, and it needs to be noted that a relation between a thickness and a width of each member and ratios among respective members are different from the actual relation and ratios. In addition, there may be portions that differ in their dimensions and ratios among the drawings, too.

First Embodiment

Figure 1:
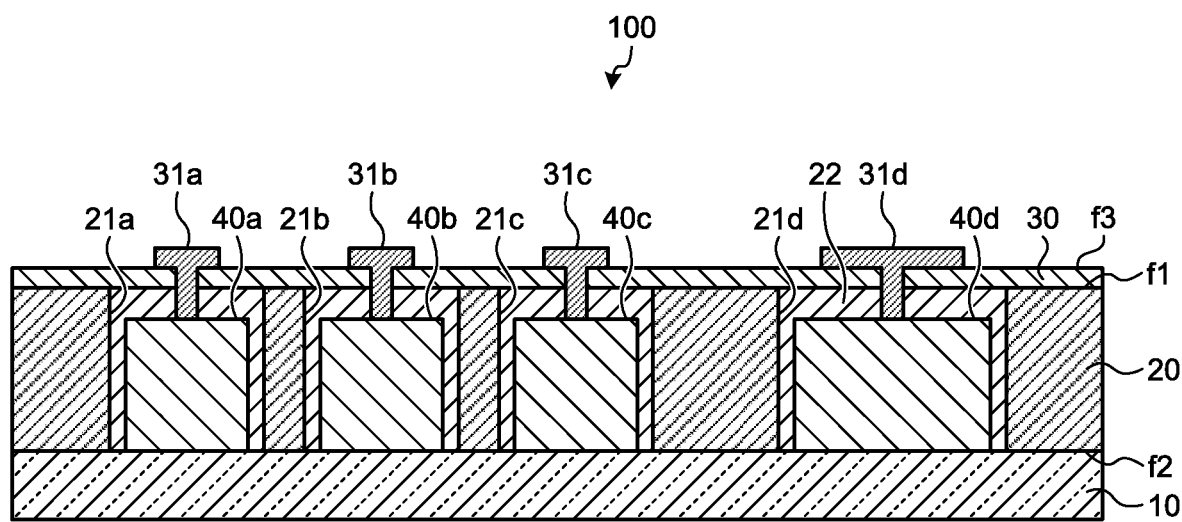
FIG. 1 is a sectional view of an electronic circuit board according to a first embodiment.

FIG. 1 is a sectional view of an electronic circuit board according to a first embodiment. An electronic circuit board 100 according to the first embodiment includes: a silicon board 20 having recessed portions 21a to 21d where electronic components 40a to 40d are mounted; a supporting board 10 that is layered over a reverse surface f2 of the silicon board 20; and an insulating protective layer 30 that is layered over a surface f1 of the silicon board 20.

The silicon board 20 is plate-shaped, and has the recessed portions 21a to 21d formed therein, the recessed portions 21a and 21d penetrating therethrough from the surface f1 to the reverse surface f2. Side faces of the recessed portions 21a to 21d are perpendicular to the surface f1 of the silicon board 20. The recessed portions 21a to 21d are formed by dry etching, preferably inductively coupled plasma (ICP) anisotropic etching. By the formation of the recessed portions 21a to 21d by ICP etching, the recessed portions 21a to 21d are able to be formed with high positional accuracy and narrow pitches.

The supporting board 10 is layered by being laminated on the reverse surface f2 side of the silicon board 20. The supporting board 10 is formed of a glass epoxy board, a flexible printed circuit board, or the like, and functions as a bottom face of the recessed portions 21a to 21d on the reverse surface f2 side thereof. The electronic components 40a to 40d are connected onto the supporting board 10 serving as the bottom face of the recessed portions 21a to 21d. The recessed portions 21a to 21d having the electronic components 40a to 40d accommodated therein have sealing resin 22 filled therein. The electronic components 40a to 40d used in this first embodiment each have a size with a length of each side thereof being equal to or less than 1 mm, for example, the so-called 0402 size (0.4 mm×0.2 mm), or the like.

The insulating protective layer 30 is layered by being laminated on a surface f1 side of the silicon board 20. Electrically conductive vias 31a to 31d are formed in the insulating protective layer 30 on the recessed portions 21a to 21d. A wiring pattern that is formed on a surface f3 side of the insulating protective layer 30 and not illustrated in the drawings is electrically connected to the electronic components 40a to 40d accommodated in the recessed portions 21a to 21d via the vias 31a to 31d.

An example, in which an insulating protective layer is stuck and via openings are formed by laser or the like, has been described above; but instead, processing, in which, after application of resin, the resin is polished so as to make the resin uniform and expose a plane, and vias up to electronic components are formed by etching of a protective layer after photolithography, may be adopted. In particular, if a photosensitive resin material is used, processing of vias by photolithography and formation of a protective film may be carried out simultaneously.

Further, if application of resin is adopted as a method of forming an insulating protective layer, the insulating protective layer may also serve as the sealing resin 22.

Next, by reference to FIG. 2A to FIG. 2E, a manufacturing process for the electronic circuit board 100 will be described. FIG. 2A to FIG. 2E are diagrams for explanation of a method of manufacturing the electronic circuit board according to the first embodiment.

Figure 2A:
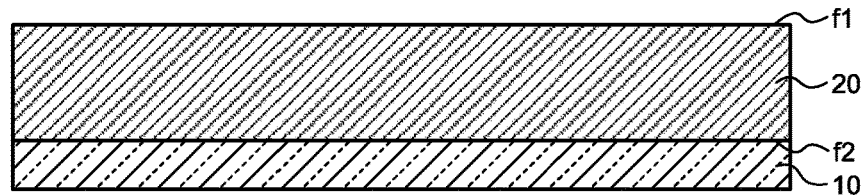
FIG. 2A is a diagram for explanation of a method of manufacturing the electronic circuit board according to the first embodiment.
Figure 2B:
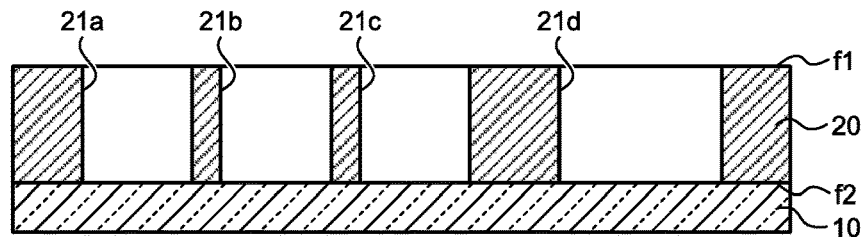
FIG. 2B is a diagram for explanation of the method of manufacturing the electronic circuit board according to the first embodiment.

As illustrated in FIG. 2A, after the supporting board 10 and the silicon board 20 are layered over each other by being laminated onto each other, the silicon board 20 is subjected to etching from the surface f1 side of the silicon board 20, and thereby the recessed portions 21a to 21d are formed. The recessed portions 21a to 21d are formed by dry etching, preferably ICP etching, by: a photoresist layer being layered over the surface f1 of the silicon board 20, and a pattern of the recessed portions 21a to 21d being formed on the photoresist layer by photolithography, with this photoresist layer being a mask. By the recessed portions 21a to 21d being etched by ICP, the recessed portions 21a to 21d having the side faces that are perpendicular to the surface f1 of the silicon board 20 are able to be formed. Since the side faces of the recessed portions 21a to 21d are perpendicular to the surface f1 of the silicon board 20, the recessed portions 21a to 21d are able to be formed with narrow pitches and mounting density thereof is able to be improved. In ICP etching, intervals between the recessed portions 21a to 21d are each able to be made about 10 μm, but for increase in mechanical strength thereof, the intervals between the recessed portions 21a to 21d are each preferably made about 20 μm. Further, insulating protective layers are preferably formed on inner wall faces of the recessed portions 21a to 21d. The insulating protective layers may be formed by, for example, formation of silicon oxide films by plasma CVD or the like in the recessed portions 21a to 21d after ICP etching. By the formation of the insulating protective layers on the inner wall faces of the recessed portions 21a to 21d, even if sizes of the recessed portions 21a to 21d are slightly larger than those of the electronic components 40a to 40d, insulation is able to be obtained.

Figure 2C:
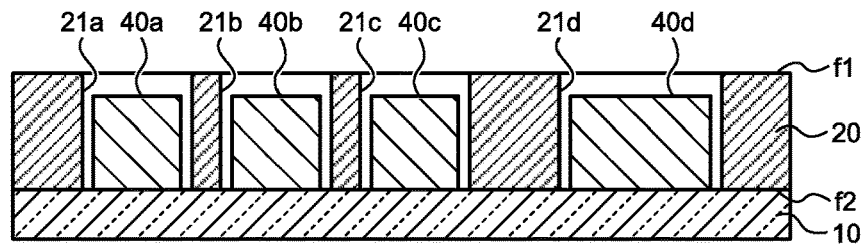
FIG. 2C is a diagram for explanation of the method of manufacturing the electronic circuit board according to the first embodiment.

After the recessed portions 21a to 21d are formed, as illustrated in FIG. 2C, the electronic components 40a to 40d are arranged to be individually accommodated in the recessed portions 21a to 21d. A joining material of solder, electrically conductive resin, or insulating resin is applied in the recessed portions 21a to 21d, the electronic components 40a to 40d are accommodated in the recessed portions 21a to 21d, and thereafter, the electronic components 40a to 40d are fixed in the recessed portions 21a to 21d by heating or the like.

Figure 2D:
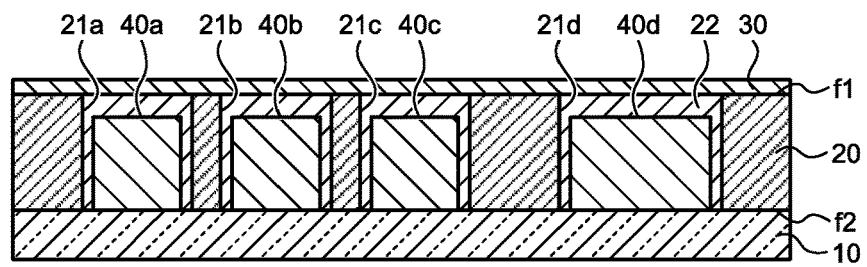
FIG. 2D is a diagram for explanation of the method of manufacturing the electronic circuit board according to the first embodiment.

After the electronic components 40a to 40d are accommodated in the recessed portions 21a to 21d, the sealing resin 22 is filled in the recessed portions 21a to 21d, and the insulating protective layer 30 is layered over the surface f1 of the silicon board 20 by being laminated thereon (see FIG. 2D).

Figure 2E:
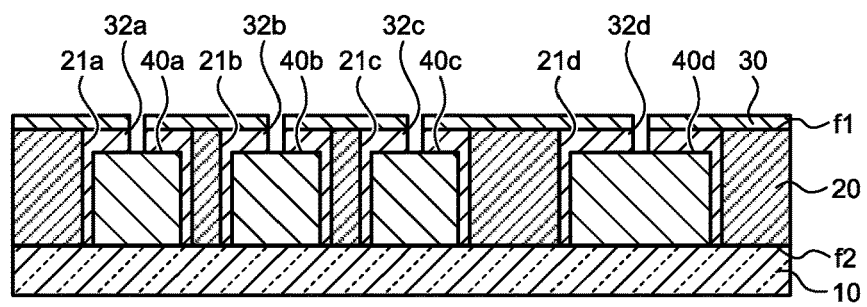
FIG. 2E is a diagram for explanation of the method of manufacturing the electronic circuit board according to the first embodiment.

After the insulating protective layer 30 is layered, as illustrated in FIG. 2E, holes 32a to 32d are made by laser or the like in the insulating protective layer 30 on the recessed portions 21a to 21d, the electrically conductive vias 31a to 31d are formed by plating being performed and/or by an electrically conductive material being filled, inside the holes 32a to 32d, and thereby the electronic circuit board 100 illustrated in FIG. 1 is manufactured.

In the first embodiment, the recessed portions 21a to 21d are formed after the silicon board 20 and the supporting board 10 are layered over each other, but the supporting board 10 may be laminated on the silicon board 20 after the recessed portions 21a to 21d are formed in the silicon board 20.

The recessed portions illustrated in FIG. 1 and FIG. 2 have recessed shapes formed by: their side faces being surrounded by the silicon board 20 having through hole portions; and the supporting board 10 serving as their bottom faces.

Figure 3:
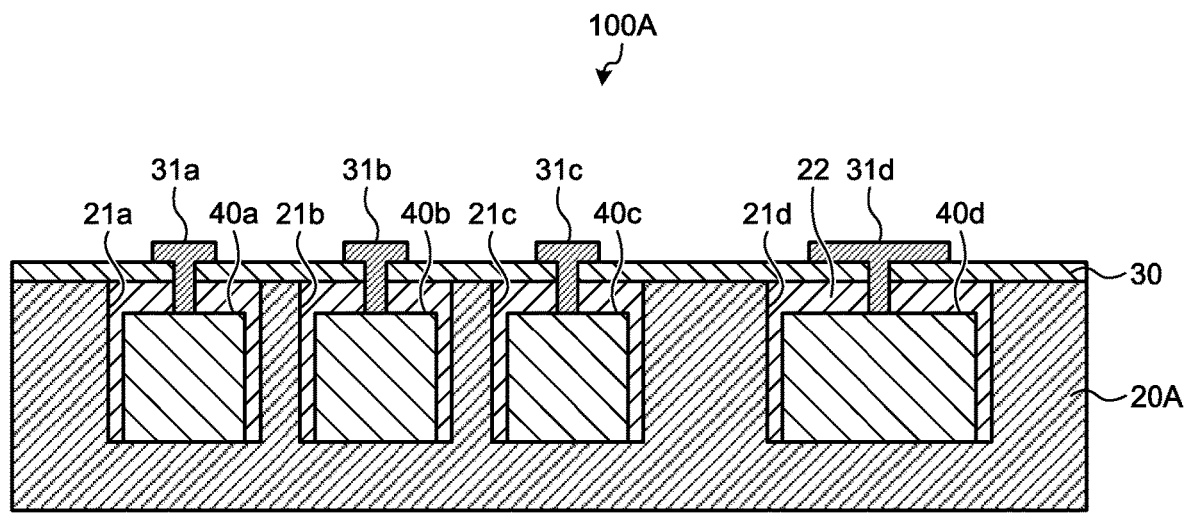
FIG. 3 is a sectional view of an electronic circuit board according to a first modified example of the first embodiment.

Further, a silicon board having bottomed recessed portions may be used in the electronic circuit board. FIG. 3 is a sectional view of an electronic circuit board according a first modified example of the first embodiment.

In FIG. 3, recessed portions have recessed shapes formed by their side faces and bottom faces being surrounded by a silicon board 20A.

An electronic circuit board 100A: includes a silicon board 20A having bottomed recessed portions 21a to 21d (with heights of the recessed portions 21a to 21d being lower than a thickness of the silicon board 20A); and does not have a supporting board. The recessed portions 21a to 21d are formed, similarly to the first embodiment, by dry etching, preferably by ICP etching, and thus side faces of the recessed portions 21a to 21d are perpendicular to a surface f1 of the silicon board 20A. Since the side faces of the recessed portions 21a to 21d are perpendicular, the recessed portions 21a to 21d are able to be formed with narrow pitches in the silicon board 20A, and mounting density of electronic components 40a to 40d is able to be improved.

Figure 4:
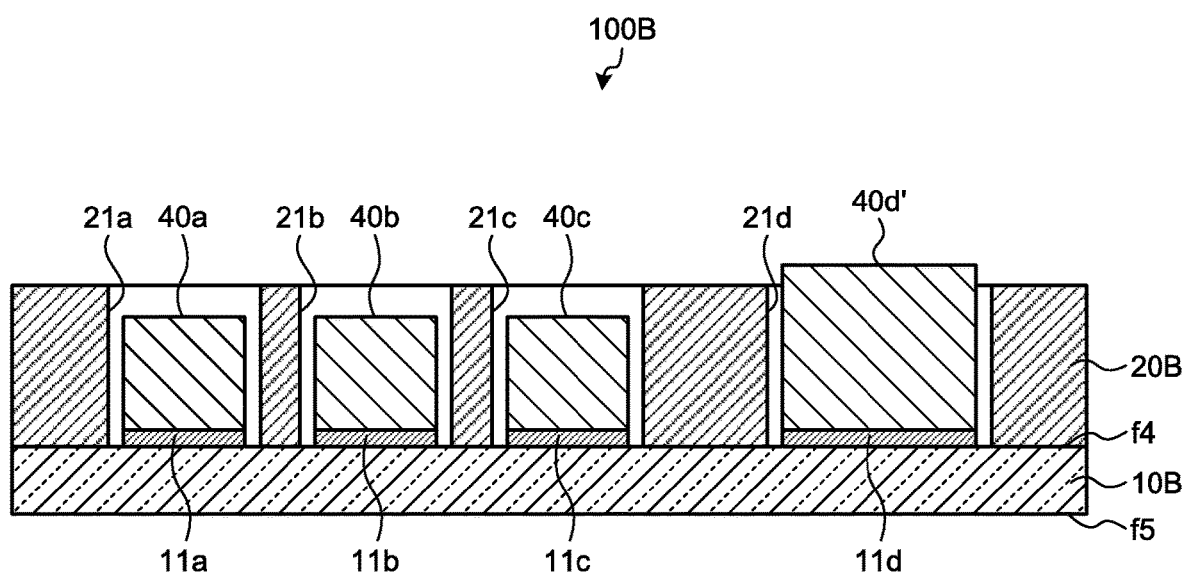
FIG. 4 is a sectional view of an electronic circuit board according to a second modified example of the first embodiment.

Further, an insulating protective layer may be not layered over the silicon board. FIG. 4 is a sectional view of an electronic circuit board according a second modified example of the first embodiment.

In an electronic circuit board 100B, bottom surface electrodes 11a to 11d electrically and mechanically connecting electronic components 40a to 40c and 40d' are formed, and a wiring pattern not illustrated in the drawings is formed; on a connected surface f4 side of a supporting board 10B (on a surface side of the supporting board 10B), the connected surface f4 side being toward a silicon board 20B. The electronic components 40a to 40c and 40d' arranged in the recessed portions 21a to 21d are connected to the bottom surface electrodes 11a to 11d via solder or electrically conductive resin. In the electronic circuit board 100B, sealing resin is not filled around the electronic components 40a to 40c and 40d' in the recessed portions 21a to 21d, and an insulating protective layer is not layered over a surface f1 of the silicon board 20B, either.

The wiring pattern formed on the connected surface f4 side of the supporting board 10B and not illustrated in the drawings is connected to the electronic components 40a to 40c and 40d' via the bottom surface electrodes 11a to 11d. A wiring pattern may be formed on a surface f5 side reverse to the connected surface f4 side of the supporting board 10B, or inside the supporting board 10B, and when the wiring pattern is formed on the reverse surface f5 side of the supporting board 10B or inside the supporting board 10B, vias are provided in the supporting board 10B, and the wiring pattern is connected to the electronic components 40a to 40c and 40d' via the vias and the bottom surface electrodes 11a to 11d. Since side faces of the recessed portions 21a to 21d in the second modified example are also perpendicular, the recessed portions 21a to 21d are able to be formed in the silicon board 20B with narrow pitches, and mounting density of the electronic components 40a to 40c and 40d' is able to be improved. Further, the electronic component 40d' having a height higher than a height of the recessed portion 21d is also able to be mounted thereon.

Second Embodiment

Figure 5:
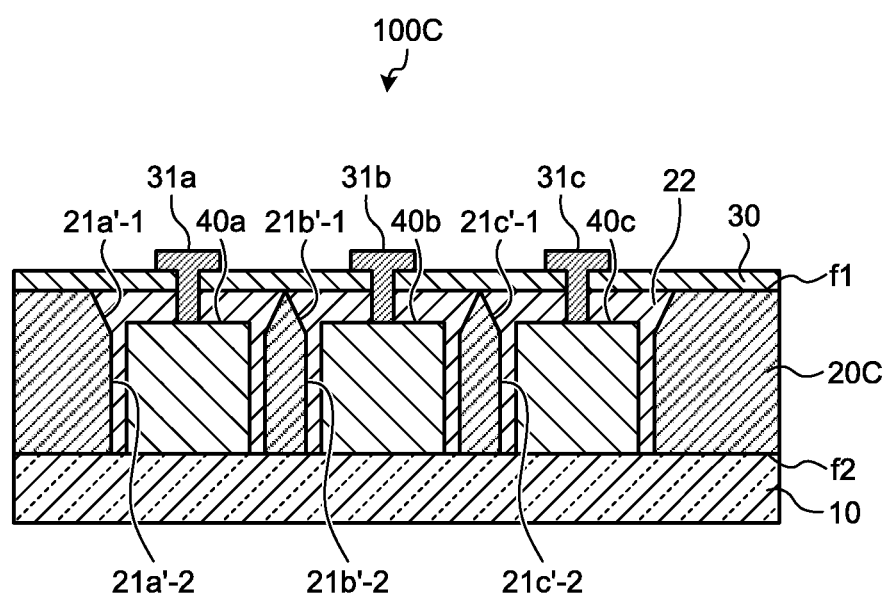
FIG. 5 is a sectional view of an electronic circuit board according to a second embodiment.

In an electronic circuit board according to a second embodiment, side faces of recessed portions have: portions tapered relatively to a surface of a silicon board; and portions that are perpendicular to the surface. FIG. 5 is a sectional view of the electronic circuit board according to the second embodiment.

An electronic circuit board 100C has a silicon board 20C having recessed portions 21a' to 21c' having electronic components 40a to 40c mounted therein. The recessed portions 21a' to 21c' respectively include: first recessed portions 21a'-1 to 21c'-1, which are formed on a surface f1 side of the silicon board 20C, and have side faces that are tapered relatively to a surface f1 of the silicon board 20C such that the first recessed portions 21a'-1 to 21c'-1 decrease in their diameters from opening sides thereof; and second recessed portions 21a'-2 to 21c'-2, which have side faces that are perpendicular to the surface f1 of the silicon board 20C.

Figure 6A:
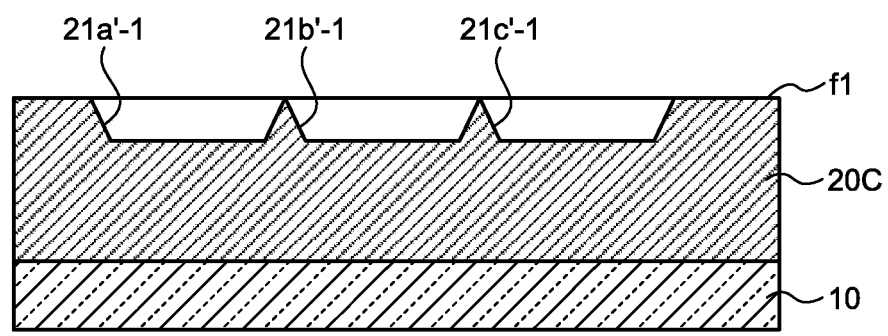
FIG. 6A is a diagram for explanation of a method of manufacturing the electronic circuit board according to the second embodiment.

The first recessed portions 21a'-1 to 21c'-1 are formed, as illustrated in FIG. 6A, by execution of tapered etching, preferably anisotropic etching through wet etching in particular, on the surface f1 of the silicon board 20C, over which a supporting board 10 has been layered.

Figure 6B:
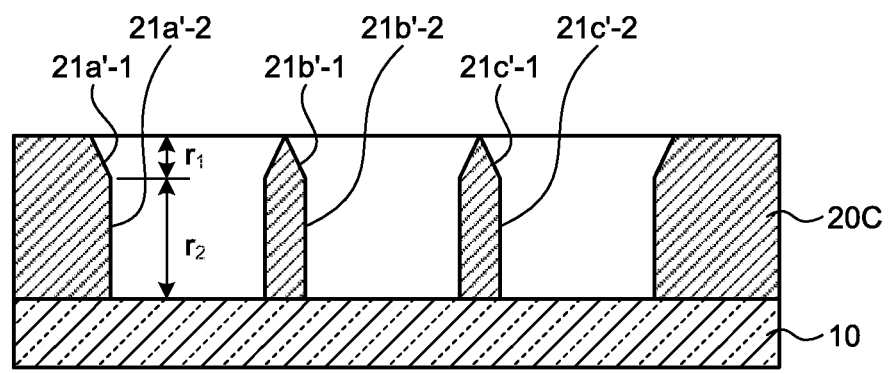
FIG. 6B is a diagram for explanation of the method of manufacturing the electronic circuit board according to the second embodiment.

The second recessed portions 21a'-2 to 21c'-2 are formed, as illustrated in FIG. 6B, by further etching through dry etching, preferably ICP etching, on the first recessed portions 21a'-1 to 21c'-1 of the silicon board 20C.

Figure 7A:
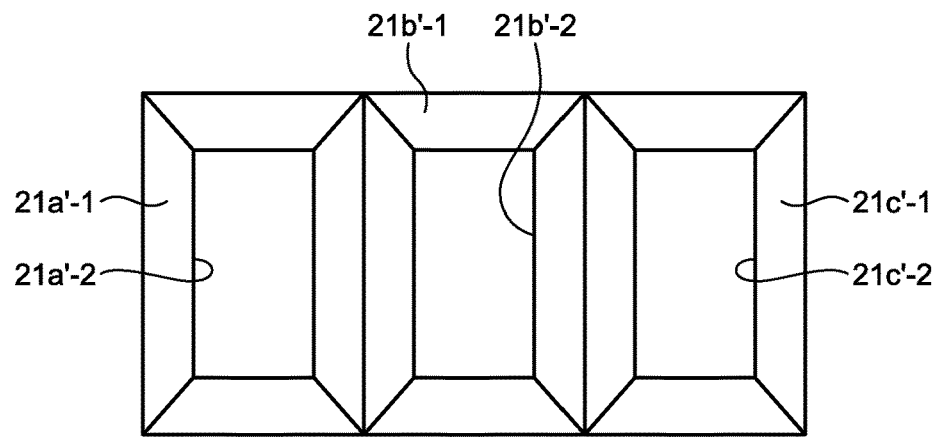
FIG. 7A is a top view of recessed portions of the electronic circuit board according to the second embodiment.
Figure 7B:
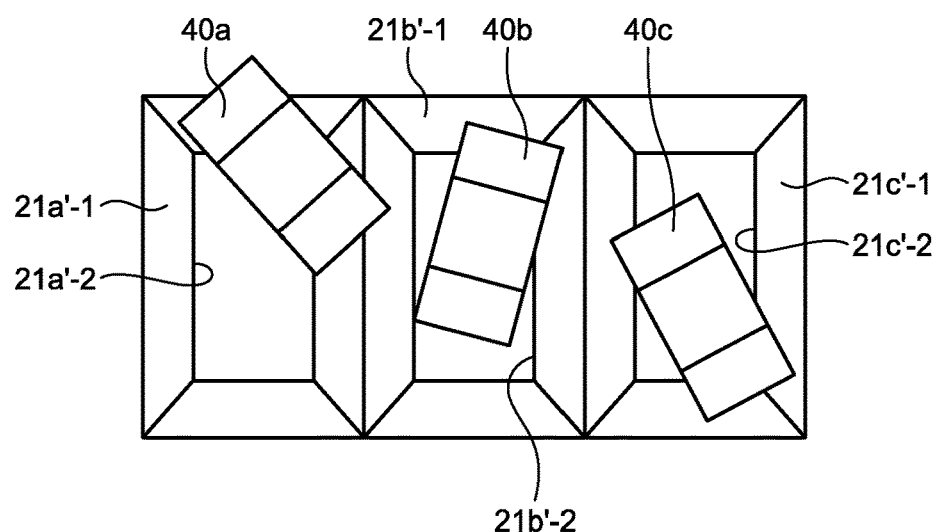
FIG. 7B is a diagram for explanation of arrangement of electronic components into the recessed portions of the electronic circuit board according to the second embodiment.
Figure 7C:
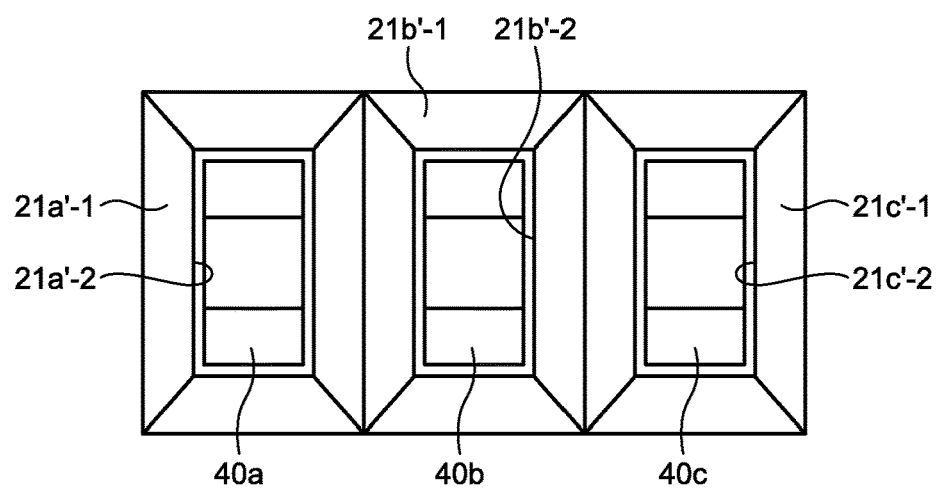
FIG. 7C is a diagram for explanation of the arrangement of the electronic components into the recessed portions of the electronic circuit board according to the second embodiment.

In the silicon board 20C having the recessed portions 21a' to 21c' configured as described above, arrangement of electronic components 40a to 40c in the recessed portions 21a' to 21c' is facilitated. FIG. 7A is a top view of the recessed portions 21a' to 21c' of the electronic circuit board 100C according to the second embodiment. FIG. 7B and FIG. 7C are diagrams for explanation of the arrangement of the electronic components 40a to 40c in the recessed portions 21a' to 21c' of the electronic circuit board 100C according to the second embodiment.

The electronic components 40a to 40c are arranged near the recessed portions 21a' to 21c' illustrated in FIG. 7A (see FIG. 7B), and the silicon board 20C is vibrated. By the silicon board 20C being vibrated, the electronic components 40a to 40c are respectively accommodated in the recessed portions 21a' to 21c'. Since the surface f1 side of the silicon board 20C in the recessed portions 21a' to 21c', on which the electronic components 40a to 40c are mounted, has the first recessed portions 21a'-1 to 21c'-1 having the side faces that are tapered relatively to the surface f1 of the silicon board 20C, the arrangement of the electronic components 40a to 40c into the recessed portions 21a' to 21c' is facilitated. This is particularly effective when the electronic components 40a to 40c are small and arrangement thereof in the recessed portions by grasping is difficult.

In terms of balance between ease of the arrangement of the electronic components 40a to 40c into the recessed portions 21a' to 21c' and mounting density of the electronic components 40a to 40c on the silicon board 20C, a height r1 of the first recessed portions 21a'-1 to 21c'-1 is preferably equal to or less than a height r2 of the second recessed portions 21a'-2 to 21c'-2, particularly equal to or less than 40% thereof.

Third Embodiment

Figure 8:
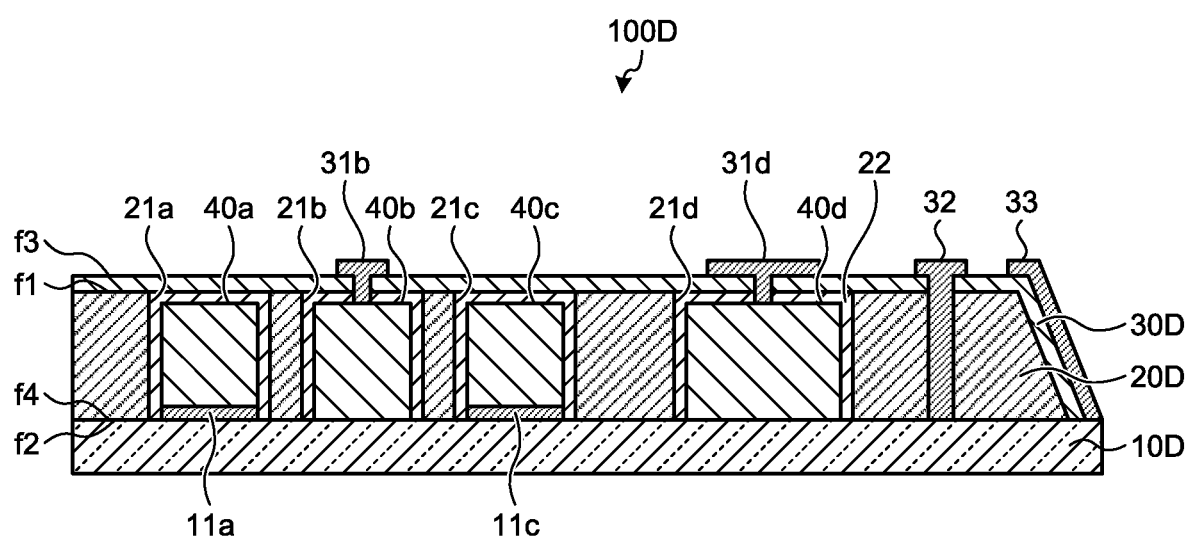
FIG. 8 is a sectional view of an electronic circuit board according to a third embodiment.

An electronic circuit board according to a third embodiment has a through electrode formed in a silicon board thereof. FIG. 8 is a sectional view of the electronic circuit board according to the third embodiment.

A silicon board 20D of an electronic circuit board 100D has a through electrode 32 formed therein, which penetrates from a surface f1 of the silicon board 20D to a reverse surface f2 thereof. A side face in a hole portion, in which the through electrode 32 is formed, has an insulating protective layer formed thereon, similarly to inner wall faces of recessed portions 21a to 21d, and the insulating protective layer insulates the silicon board 20D and the through electrode 32 from each other. Further, a side surface of the silicon board 20D has a side surface electrode 33 formed thereon, and the side surface electrode 33 also functions as a through electrode by being formed from the surface f1 of the silicon board 20D to the reverse surface f2 thereof.

On a connected surface f4 side of a supporting board 10D, the connected surface f4 side being toward the silicon board 20D, bottom surface electrodes 11a and 11c, to which electronic components 40a and 40c are electrically and mechanically connected, are formed, and the bottom surface electrodes 11a and 11c are connected to a wiring pattern, which is formed on the connected surface f4 side of the supporting board 10D and not illustrated in the drawings. The electronic components 40a and 40c arranged in the recessed portions 21a and 21c are respectively connected to the bottom surface electrodes 11a and 11c via solder or electrically conductive resin.

An insulating protective layer 30D is layered by being laminated on a surface f1 side of the silicon board 20D. The insulating protective layer 30D is also layered on the side surface of the silicon board 20D, the side surface being where the side surface electrode 33 is formed, and insulates the silicon board 20D and the side surface electrode 33 from each other. Electrically conductive vias 31b and 31d are formed in the insulating protective layer 30D on the recessed portions 21b and 21d. The electrically conductive vias 31b and 31d are respectively connected electrically to the electronic components 40b and 40d accommodated in the recessed portions 21b and 21d, and are connected to a wiring pattern, which is formed on a surface f3 side of the insulating protective layer 30D and is not illustrated in the drawings.

The through electrode 32 and the side surface electrode 33 are connected to: the wiring pattern formed on the connected surface f4 side of the supporting board 10D; and the wiring pattern formed on the surface f3 side of the insulating protective layer 30D.

The electronic circuit board 100D according to the third embodiment enables mounting density of the electronic components 40a to 40d to be improved, since the side faces of the recessed portions 21a to 21d are perpendicular to the surface of the silicon board 20D. Further, since the wiring pattern formed on the supporting board 10D and the wiring pattern formed on the insulating protective layer 30D are connected to each other via the through electrode 32 and the side surface electrode 33, wiring freedom is able to be improved.

Fourth Embodiment

Figure 9:
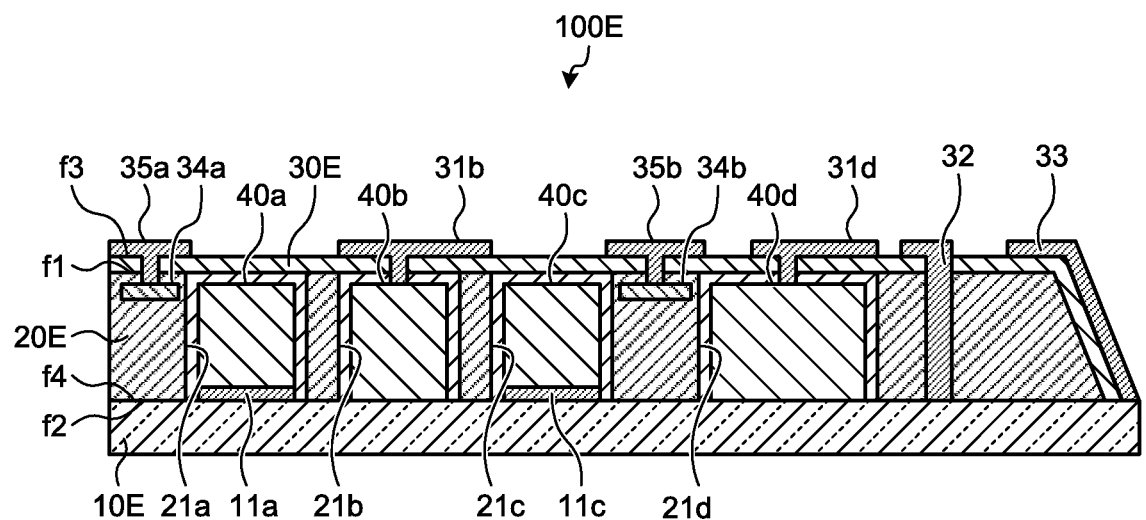
FIG. 9 is a sectional view of an electronic circuit board according to a fourth embodiment.

An electronic circuit board according to a fourth embodiment has semiconductor circuits formed on a silicon board thereof. FIG. 9 is a sectional view of the electronic circuit board according to the fourth embodiment.

A silicon board 20E of an electronic circuit board 100E has semiconductor circuits 34a and 34b formed at a surface f1 side thereof. The semiconductor circuits 34a and 34b are formed by semiconductor processes. A silicon wafer having the plural semiconductor circuits 34a and 34b formed thereon is subjected to singulation and formed into the silicon board 20E, and thereafter, recessed portions 21a to 21d are formed by ICP etching.

An insulating protective layer 30E is layered by being laminated on the surface f1 side of the silicon board 20E, and electrically conductive vias 31b, 31d, 35a, and 35b are formed in the insulating protective layer 30E on the recessed portions 21b and 21d and on the semiconductor circuits 34a and 34b. A wiring pattern, which is formed on a surface f3 side of the insulating protective layer 30E and not illustrated in the drawings, is electrically connected to electronic components 40b and 40d and the semiconductor circuits 34a and 34b, via the vias 31b, 31d, 35a, and 35b.

On a connected surface f4 side of a supporting board 10E, the connected surface f4 side being toward the silicon board 20E, bottom surface electrodes 11a and 11c, to which the electronic components 40a and 40c are electrically and mechanically connected, are formed, and the bottom surface electrodes 11a and 11c are connected to a wiring pattern, which is formed on the connected surface f4 side of the supporting board 10E and not illustrated in the drawings. The electronic components 40a and 40c arranged in the recessed portions 21a and 21c are respectively connected to the bottom surface electrodes 11a and 11c via solder or electrically conductive resin, and are connected to a wiring pattern, which is formed on the surface f3 side of the insulating protective layer 30E, via the through electrode 32 and the side surface electrode 33.

The electronic circuit board 100E according to the fourth embodiment has the semiconductor circuits 34a and 34b in the silicon board 20E, and thus downsizing and integration of the electronic circuit board 100E are enabled as there is no need for semiconductor circuits to be newly provided therein.

Fifth Embodiment

Figure 10:
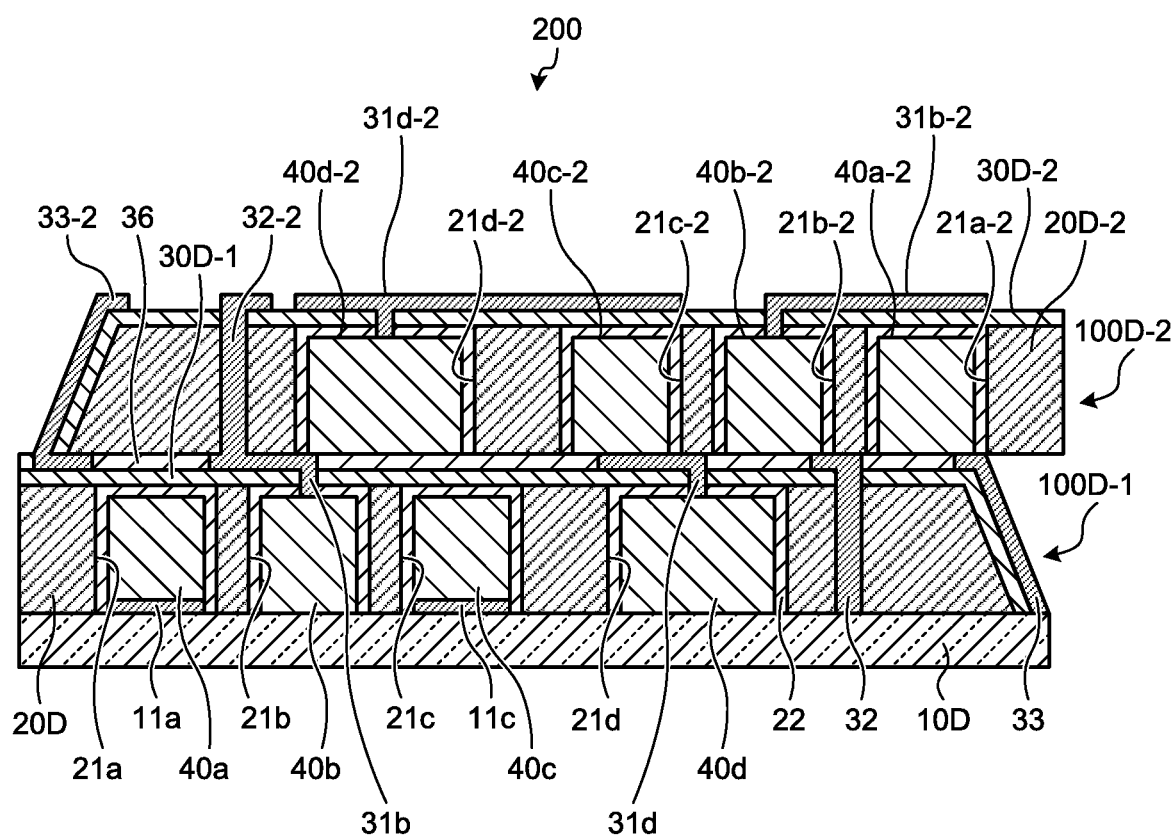
FIG. 10 is a sectional view of a laminated board according to a fifth embodiment.

A fifth embodiment is a laminated board having electronic circuit boards layered over each other. FIG. 10 is a sectional view of the laminated board according to the fifth embodiment.

A laminated board 200 has a first electronic circuit board 100D-1 and a second electronic circuit board 100D-2 that are layered over each other. The first electronic circuit board 100D-1 has a configuration similar to that of the electronic circuit board 100D according to the third embodiment, and has an intermediate layer 36 having an insulating function, such as a resist layer, the intermediate layer 36 being layered on a surface of an insulating protective layer 30D-1.

The second electronic circuit board 100D-2 has an insulating protective layer layered therein, instead of the supporting board 10D on a reverse surface f2 side of the silicon board 20D according to the third embodiment. The second electronic circuit board 100D-2 is able to be manufactured by formation of vias 31b-2 and 31d-2, a through electrode 32-2, and a side surface electrode 33-2, after an insulating protective layer 30D-2 is layered and electronic components 40a-2 to 40d-2 are arranged in recessed portions 21a-2 to 21d-2, after the recessed portions 21a-2 to 21d-2 are formed in a silicon board 20D-2.

Since the laminated board 200 has the first electronic circuit board 100D-1 and the second electronic circuit board 100D-2 that are layered over each other, mounting density of electronic components is able to be improved.

Figure 11:
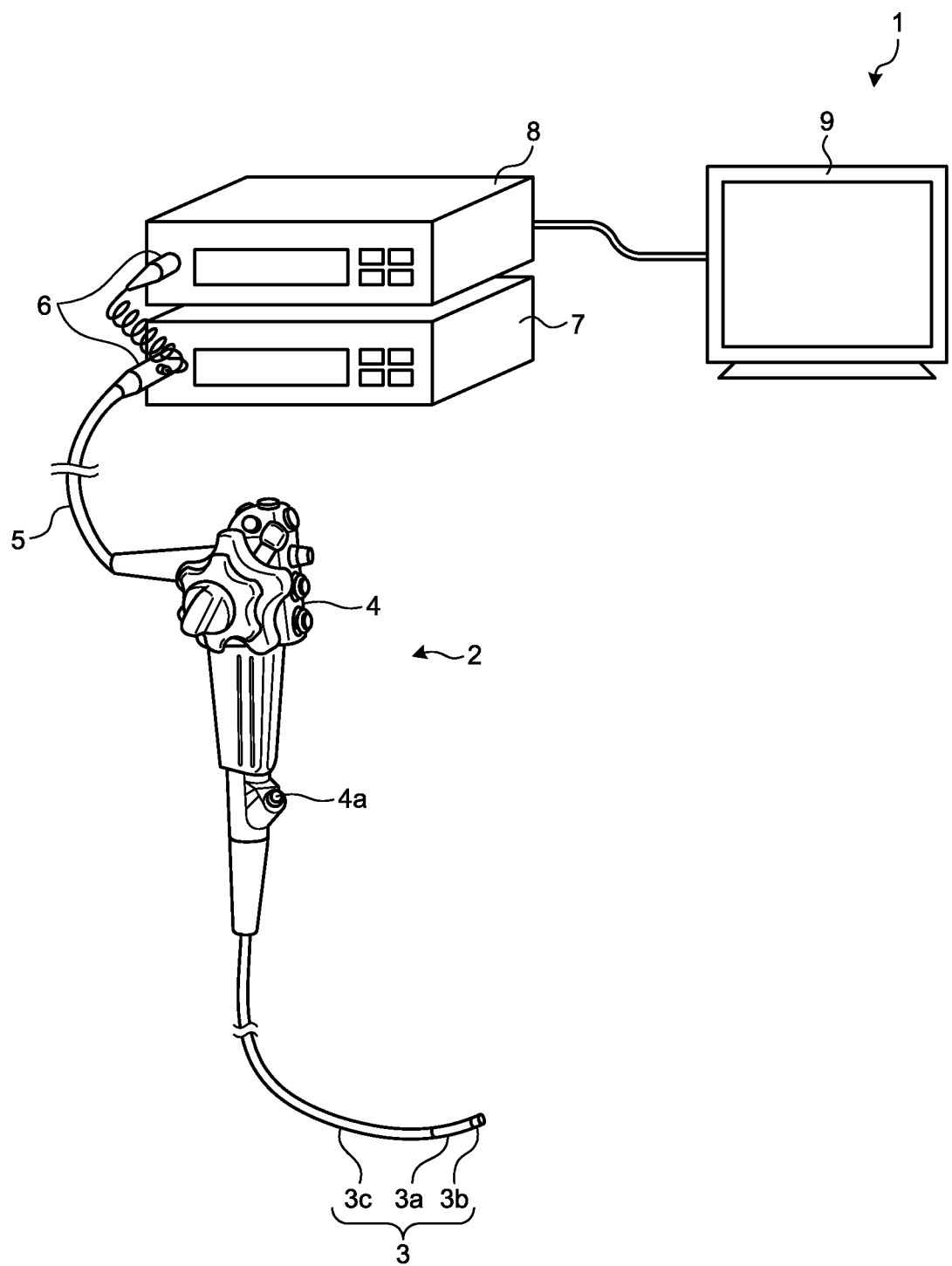
FIG. 11 is a diagram schematically illustrating an overall configuration of an endoscope system, in which the laminated board according to the fifth embodiment is used.
Figure 12:
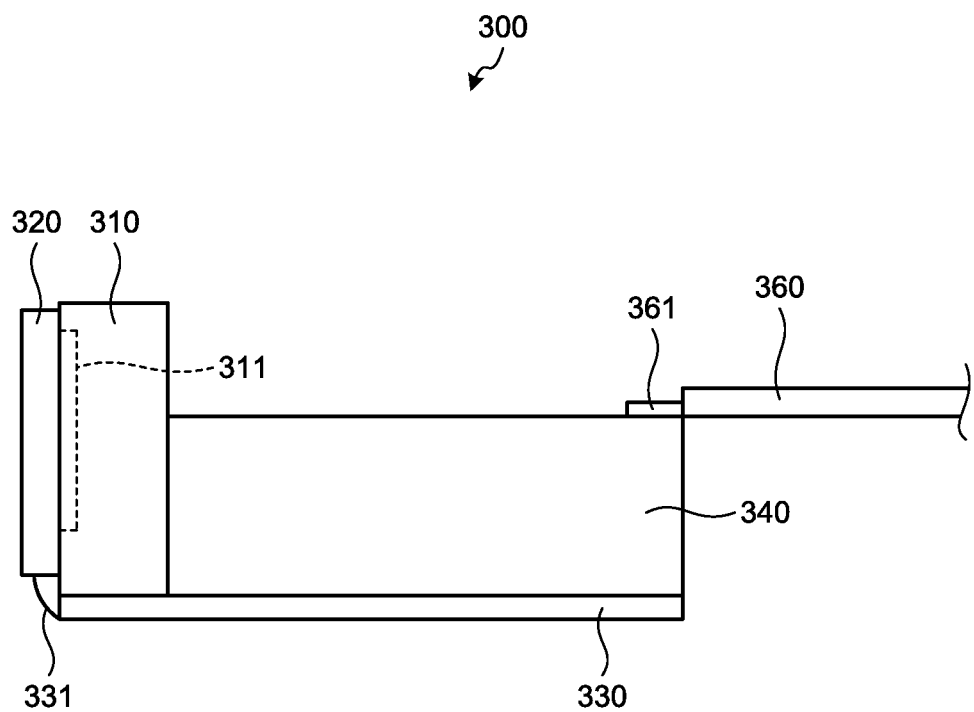
FIG. 12 is a side view of an imaging unit used in an endoscope of FIG. 11.

The laminated board according to the fifth embodiment is able to be suitably used in an imaging unit of an endoscope system described later. FIG. 11 is a diagram schematically illustrating an overall configuration of the endoscope system, in which the laminated board according to the fifth embodiment is used. FIG. 12 is a side view of the imaging unit used in an endoscope of FIG. 11.

As illustrated in FIG. 11, an endoscope system 1 includes an endoscope 2, a universal cord 5, a connector 6, a light source device 7, a processor (control device) 8, and a display device 9.

The endoscope 2 captures an in-vivo image of a subject and outputs an imaging signal, by insertion of an insertion unit 3 into the subject. A cable inside the universal cord 5 is extended to a distal end of the insertion unit 3 of the endoscope 2, and is connected to the imaging unit provided at a distal end portion 3b of the insertion unit 3.

The connector 6 is provided at a proximal end of the universal cord 5, is connected to the light source device 7 and the processor 8, executes predetermined signal processing on the imaging signal (output signal) output by an imaging unit 300 at the distal end portion 3b connected to the universal cord 5, executes analog/digital conversion (A/D conversion) on the imaging signal, and outputs the converted imaging signal as an image signal.

The light source device 7 is, for example, configured by use of a white LED. Pulsed white light lighted by the light source device 7 serves as illumination light to be emitted toward the subject from the distal end of the insertion unit 3 of the endoscope 2 via the connector 6 and the universal cord 5.

The processor 8 executes predetermined image processing on the image signal output from the connector 6, and controls the whole endoscope system 1. The display device 9 displays thereon the image signal processed by the processor 8.

An operating unit 4 provided with various buttons and knobs, through which endoscopic functions are operated, is connected at a proximal end side of the insertion unit 3 of the endoscope 2. The operating unit 4 has a treatment tool insertion opening 4a provided therein, through which a treatment tool, such as biopsy forceps, an electric knife, or an inspecting probe, is inserted in a body cavity of the subject.

The insertion unit 3 includes: the distal end portion 3b where the imaging unit 300 is provided; a bent portion 3a, which is connected consecutively to a proximal end side of the distal end portion 3b and is freely bendable in an up-down direction; and a flexible tube portion 3c, which is connected consecutively to a proximal end side of this bent portion 3a. The bent portion 3a is bent in the up-down direction by operation on a bending operation knob provided in the operating unit 4, and is freely bendable in two directions, for example, upward and downward, in association with pull and relaxation of a bending wire inserted through the insertion unit 3.

A light guide that transmits the illumination light from the light source device 7 is arranged in the endoscope 2, and an illumination window is arranged at an illumination light emission end of the light guide. This illumination window is provided at the distal end portion 3b of the insertion unit 3, and the illumination light is emitted toward the subject from this illumination window.

The imaging unit 300 provided at the distal end portion 3b of the endoscope 2 includes, as illustrated in FIG. 12: an imaging element 310 having a light receiving unit 311 that photoelectrically converts incident light and generates an electric signal; an optical member 320 that seals the light receiving unit 311; a flexible printed circuit board (hereinafter, referred to as "FPC board") 330; and a hard board 340. The laminated board 200 has functions of the FPC board 330 and the hard board 340, of the imaging unit 300.

The imaging element 310 includes an electrode pad not illustrated in the drawings, around the light receiving unit 311 formed at a central portion of a principal surface thereof, and a bump (not illustrated in the drawings) made of solder or the like is formed on the electrode pad.

The optical member 320 is formed of a material having excellent optical properties, such as glass, and is adhered to the imaging element 310 by an adhesive.

The FPC board 330 has an insulating base and a wiring layer formed inside or on a surface of the base, and an inner lead is connected to the electrode pad of the imaging element 310, the inner lead being a part of the wiring layer, the part being exposed from the base. A connected portion between the inner lead and the electrode pad is sealed by a sealing resin 331. The FPC board 330 extends from a side surface (bottom surface) side to a reverse surface side of the imaging element 310, and the hard board 340 having plural conductor layers is connected onto an extended surface of the FPC board 330. A conductor 361 of a cable 360 is connected to a proximal end side of the hard board 340.

By use of the laminated board 200 according to the fifth embodiment in the imaging unit 300, decrease in diameter and decrease in length of the imaging unit are enabled.

According to the present disclosure, an electronic circuit board is able to be downsized even when many electronic components are mounted thereon, because mounting density of electronic components thereon is able to be improved.

Additional advantages and modifications will readily occur to those skilled in the art. Therefore, the disclosure in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An electronic circuit board, comprising:
   a silicon board having a plate shape, the silicon board comprising
   a plurality of recessed portions, each of the plurality of recessed portions penetrating completely through the silicon board from a surface to an opposed reversed surface, at least one side face of each of the plurality of recessed portions being perpendicular to the surface of the silicon board;
   a plurality of electronic components, an electronic component of the plurality of electronic components being mounted in each of the plurality of recessed portions;
   a supporting board layered over the reverse surface of the silicon board;
   a sealing resin completely filled in a respective recessed portion of the plurality of recessed portions from the surface to the opposed reverse surface of the silicon board to embed and fix the electronic components in the sealing resin; and
   an insulating protective layer that is layered over the surface of the silicon board and a surface of the sealing resin filling each of the plurality of recessed portions;

wherein
an electrically conductive via is formed in each of the plurality of recessed portions, each electrically conductive via being formed through the insulating protective layer and sealing resin to electrically connect each of the plurality of electronic components to a wiring pattern formed on the insulating protective layer.

2. The electronic circuit board according to claim 1, wherein at least one of the plurality of recessed portions comprises:
a first recessed portion provided on the surface of the silicon board includes a tapered side face such that the first recessed portion is reduced in diameter from an opening side of the first recessed portion; and
a second recessed portion including the at least one side face perpendicular to the surface of the silicon board.

3. The electronic circuit board according to claim 1, wherein an additional insulating protective layer is provided on an inner wall face of at least one of the plurality of recessed portions.

4. The electronic circuit board according to claim 1, wherein the silicon board includes a semiconductor circuit.

5. A laminated board, comprising:
the electronic circuit board according to claim 1 layered therein.

6. A method of manufacturing the electronic circuit board according to claim 1, the method comprising:
forming, by etching the silicon board, the plurality of recessed portions in the silicon board, the plurality of recessed portions including at least one side face perpendicular to the surface of the silicon board;
arranging the electronic component of the plurality of electronic components in the respective ones of the plurality of recessed portions; and
embedding and fixing the plurality of electronic components in respective ones of the plurality of recessed portions with the sealing resin.

7. The method of manufacturing the electronic circuit board according to claim 6, wherein the forming comprises:
forming a first recessed portion on the surface of the silicon board, the first recessed portion including a tapered side face such that the first recessed portion is reduced in diameter from an opening side of the first recessed portion; and
forming a second recessed portion including the at least one side face perpendicular to the surface of the silicon board.

8. The method of manufacturing the electronic circuit board according to claim 7, wherein in the arranging, after the plurality of electronic components are mounted on the silicon board, vibrating the silicon board to drop the plurality of electronic components into a respective one of the plurality of recessed portions.

* * * * *